United States Patent [19]

Stephens et al.

[11] Patent Number: 4,926,702

[45] Date of Patent: May 22, 1990

[54] SAMPLE PRESENCE DETECTOR FOR AUTOMATIC SAMPLE INJECTOR

[75] Inventors: Donald E. Stephens, Palo Alto; Manfred W. Unterbusch, Sunnyvale, both of Calif.

[73] Assignee: Beckman Instruments, Inc., Fullerton, Calif.

[21] Appl. No.: 98,573

[22] Filed: Sep. 18, 1987

[51] Int. Cl.⁵ ............................................. G01N 1/14
[52] U.S. Cl. ............... 73/864.83; 73/863.73; 73/863.01
[58] Field of Search ................... 73/864–884, 73/864.83, 863.73, 863.01

[56] References Cited

U.S. PATENT DOCUMENTS 3,504,799  4/1970  Ogle .......................... 73/864.83 X
4,059,009  11/1977  Ball et al. ..................... 73/864.83
4,444,066  4/1984  Ogle et al. ..................... 73/864.84

Primary Examiner—Tom Noland
Attorney, Agent, or Firm—William H. May; Paul R. Harder; Wen Liu

[57] ABSTRACT

A detector for detecting the presence of an electrically conductive sample solution in a sample injection metering valve by electrical sensing the leading edge of the sample solution, wherein the amount of sample solution in excess of the metered amount required to cause detection is minimized. A conductive probe is positioned on the valve body just downstream of the sample metering passage of the valve, the probe being electrically insulated from the valve body. The probe and valve body form electrodes which will detect the arrival of the leading edge of a conductive sample solution which completes a conductive circuit between the electrodes.

20 Claims, 4 Drawing Sheets 4,926,702

SAMPLE PRESENCE DETECTOR FOR AUTOMATIC SAMPLE INJECTOR

BACKGROUND OF THE INVENTION

This invention relates to chromatography and more particularly to a sample injection apparatus and process which enables rapid injection of sequential chromatographic samples with minimal overfill.

SUMMARY OF THE PRIOR ART

Existing automatic sample injector systems utilize rate of transfer and time duration to control movement of samples from storage coils into the metering loop on the sample injector valve. These systems require the application of a large excess of sample to insure filling of the metering loop on the injector valve.

Other sample injector systems employ detection schemes to control the transfer of samples into the metering loop of an injector valve. Some of these employ photoelectric detectors which, while being serviceable in systems utilizing non-polar solvents, are sensitive to entrained air. Others also employ conductivity cells, but these conductivity cells are located in the plumbing external to the valve, requiring that the necessary overfill be extended to include an extra amount of sample which must fill that volume of the system beyond the valve to the conductivity cell detector.

The disclosed detection cell apparatus in combination with the flushing and sample injection process herein disclosed is an improvement upon the sample injection valve disclosed in Ogle et al. U.S. Pat. No. 4,444,066, the disclosure of that patent constituting prior art.

SUMMARY OF THE INVENTION

A conductivity detector connected in intimate proximity to a sample injection valve enables rapid sample injection into the chromatographic column with minimum sample overfill required. The injection valve includes a housing or stator having an interior moving member or rotor. The valve rotor includes passageways. The passageways rotate into and out of registry with complementary valve conduits connected to wells within the valve housing or stator. These passageways include a sample trapping passageway, an exit passageway, and a chromatographic column passageway. The rotor is placed in a first flush and sample injecting position with respect to the stator. In this first position and during a flush cycle, the chromatographic column connects across the valve rotor at the chromatographic column passageway between two of the inlet and outlet conduits for passage of buffering solution. The remaining two conduits on the inlet side and the remaining two conduits on the outlet side are connected by the respective sample trapping passageway and exit passageway to a circuit independent of the chromatographic column. Flushing all conduits with deionized water occurs in a direction towards and through the sample storage. For the sample transfer, rinse solution is cut off, the circuit is maintained filled with deionized water and a sample holding mechanism with a full sample is indexed into the circuit. Flow is reversed through the exit passageway and valve sample trapping passageway under suction from a peristaltic pump. Sample transfer occurs and continues until the leading edge of the sample begins to leave the sample trapping passageway in the valve rotor. A dielectrically insulated conductive conduit, typically a stainless steel capillary, penetrates into the one of the entrance wells from the sample trapping passageway. Upon entrance of the leading edge of the sample to the entrance well, a circuit is completed between the injection valve housing or stator and insulated conductive conduit. The completed circuit through an amplified signal halts pumping, trapping the leading edge of the sample at the sample trapping passageway within the valve rotor. The rotor then indexes to the insertion position, and the sample is sequentially injected through the recently flushed path into the column for conventional chromatographic analysis.

OTHER OBJECTS AND ADVANTAGES

An object of this invention is to disclose in combination with an injection valve utilized in chromatographic circuit, a detector for trapping a sample with minimum overfill. A valve rotor moves a sample trapping passageway into registry with a chromatographic injection circuit. The sample trapping passageway discharges during sample injection to a conduit and well penetrated by a conductive conduit, typically a stainless steel capillary. When sample is injected through the sample trapping channel, the leading edge of the sample passes into the well, completes a signal generating electric circuit between the capillary and valve, and stops injection pumping. Thereafter, the valve rotor indexes within the valve stator to an injection position in series with the chromatographic column, the sample is injected, and conventional analysis follows.

An advantage of the apparatus and process is that minimal overfill of the sample is required. Specimen is conserved.

A further advantage of apparatus and process is that run time between sequential samples is reduced.

An additional object of this invention is to incorporate the sample trapping passageway into a prior art circuit which is readily flushed by rinse solution of previous sample. According to this aspect of the invention, after sample injection, the sample trapping passageway indexes into a rinse circuit. A deionizing solution washes the sample trapping passageway and all conduits through which the sample passes. There results the ability of the sample trapping passageway and associated injection circuit to receive sequential specimens for analysis.

BRIEF DESCRIPTION OF THE DRAWINGS

The detector described herein constitutes a direct improvement of the sample injector system described in Ogle et al. U S. Pat. No. 4,444,066 issued 4/24/84 to the assignee herein. The operation of that system, as modified by the addition of the sample presence detector of FIG. 5 is described in FIGS. 1A, 1B, 1C, 2, 3 and 4.

SYSTEM SCHEMATIC

Figure 1A:
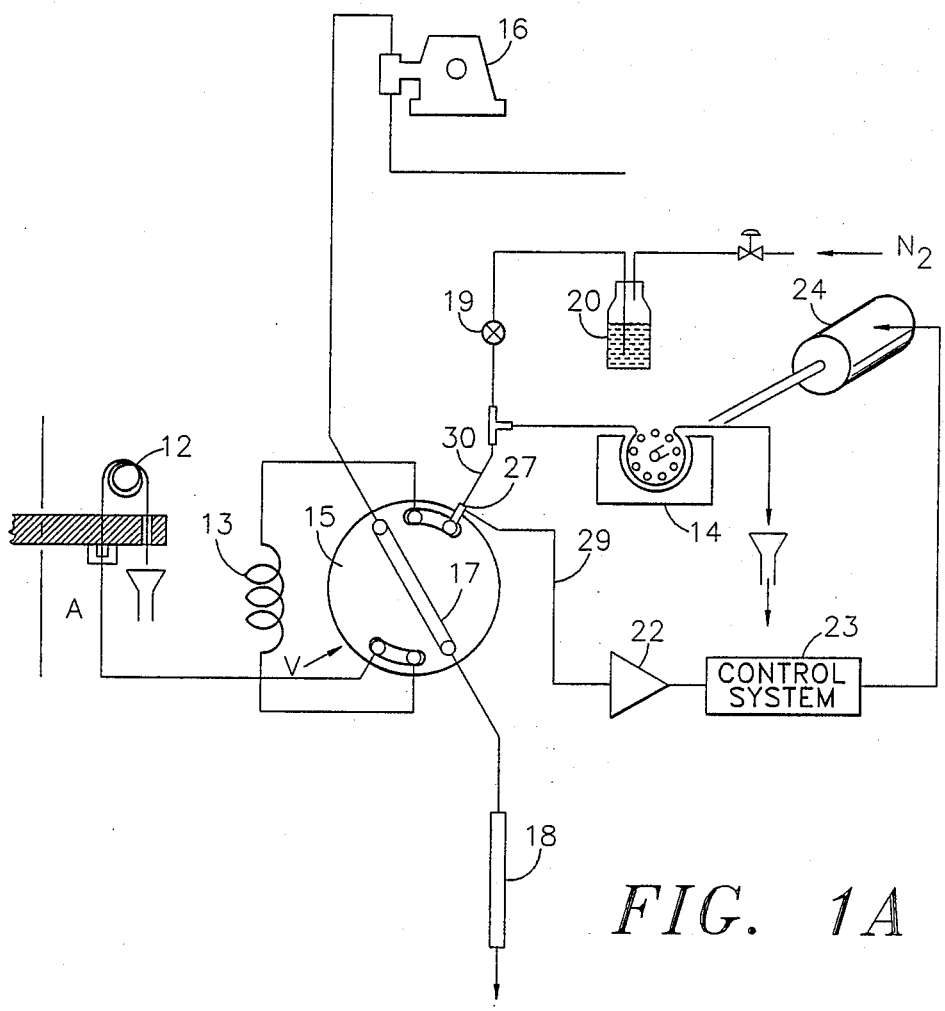
FIG. 1A is an overall circuit schematic of the invention illustrating the chromatographic circuitry.
Figure 1B:
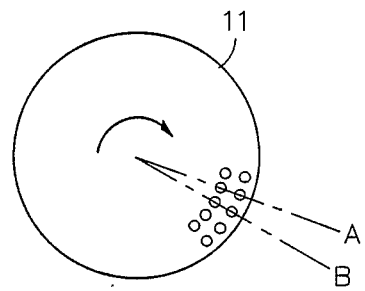
FIG. 1B is a schematic of a rotary table for dispensing sequential samples.

Referring to FIG. 1A, the complete sample injection system comprises a rotary storage table 11 having capacity to store 48 separate sample storage coils, positioning each sample storage coil in sequence over two operating stations—A and B—shown in the inset of FIG. 1B. Upon demand, the sample is drawn from its storage coil 12 into metering loop 13 by the operation of peristaltic pump 14. The routing of fluid through the injector valve V. into the metering loop 13, and subsequently into the chromatographic stream is controlled by the rotation of the injector shear-face rotor 15 which contains the passageways shown.

For the purposes of the schematics of FIGS. 1A, 2, 3 and 4, only the shear face rotor 15 will be illustrated. Reference to the stator construction is set forth in FIG. 5 and to prior art Ogle et al. U.S. Pat. No. 4,444,066.

FIG. 1A shows this valve rotor 15 in position to direct column effluent from the column pump 16, through the valve bypass passageway 17 in the shear-face rotor 15 onto the chromatographic column 18. In this valve position, the sample metering loop is connected to the sample table and to the peristaltic pump. The transfer of the sample, cleaning and drying of the storage coil, and injection of the sample is accomplished by a series of operations in a programmed schedule. These operations are described in the following discussion. For purposes of clarity, only those elements of FIG. 1A that pertain to the operation being described will be included in subsequent FIGS. 1C, 3, 4 and 5.

FLUSH CYCLE

Figure 2:
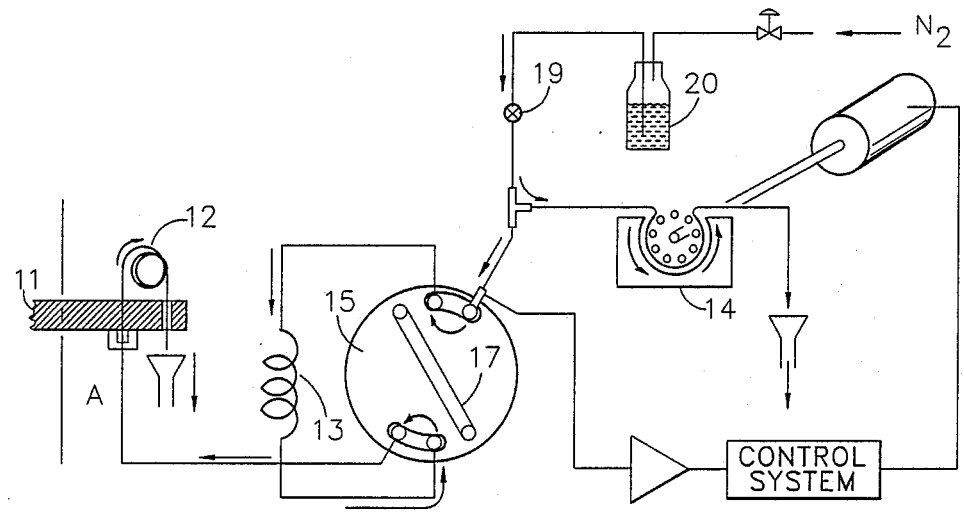
FIG. 2 is a partial schematic similar to FIG. 1A illustrating the flushing cycle of this invention.

Referring to FIG. 2 and since a clean system is critical to the operation of the detector the Flush Cycle will be described first. This operation presumes that the sample which was contained in the storage coil on the table has already been injected. Flush proceeds as follows:

Solenoid operated flush valve 19 is opened, permitting deionized water stored under nitrogen pressure in reservoir 20 to flow in the direction shown—through the sample metering loop 13, through the sample storage coil 12 and out to waste. At the same time, the transfer pump 14 runs, ensuring that the pump is thoroughly primed with deionized water. The Flush Cycle is a timed operation that is under analyzer process control. By the end of this cycle, the system is completely filled with deionized water. During this cycle the column pump is connected to the column by the injector valve bypass passage 17 as shown in FIG. 1. Column 18 has buffering solution forced through the column by pump 16 through passageway 17 (See FIG. 1A)

COIL DRY

Figure 1C:
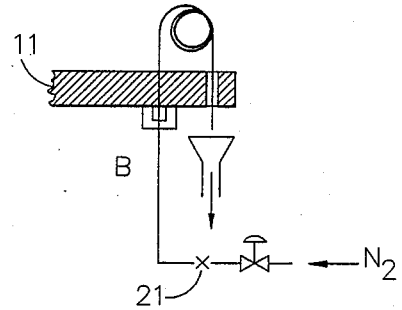
FIG. 1C is a sectional schematic through rotary table of FIG. 1B illustrating a circuit for drying the sample holder.

Referring to FIG. 1C. the sample storage table is indexed one position. This causes the storage coil 12 that has just been flushed to advance from station A to station B. At this time, solenoid valve 21 opens, admitting nitrogen to the sample storage coil. The deionized water in the storage coil is forced out of the coil to drain and the coil is blown dry.

Also, as the sample table was indexed the storage coil for the next sample to be injected was moved into position at station A. Coil Dry is a timed operation under analyzer process control. During this period, the column pump remains connected to the chromatographic column via the bypass passage 17 as shown in FIG. 1A.

SAMPLE TRANSFER

Figure 3:
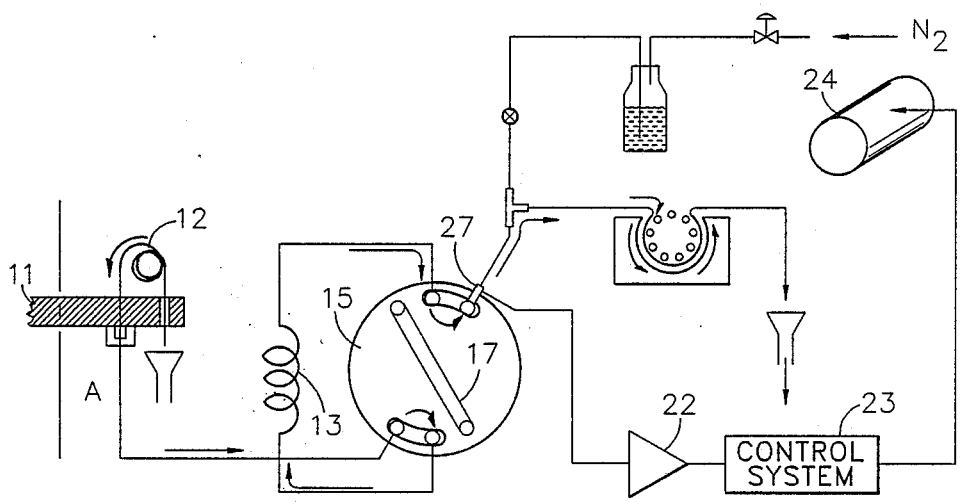
FIG. 3 is a partial schematic similar to FIG. 1A illustrating the sample transfer of this invention.

Referring to FIG. 3, the storage coil containing the sample to be injected is now at station A of the storage table (see FIG. 1B). The entire system, from the table interface at station A through the sample metering loop 13 and the sample transfer pump 14 is filled with deionized water. The sample in the storage coil 12 is separated from the table interface by a section of air in the vertical portion of the capillary in the storage coil above the table interface. This slug of air is the result of the prior art coil loading procedure, and is purposely left in place to prevent the sample from siphoning out of the storage loop while it awaits its turn to be transferred to the sample metering loop. Under process control, the transfer pump 14 is turned on causing the flush liquid, followed by the air slug and the sample to move in the direction shown toward valve V. The air slug, followed by the leading edge of the sample enters the injector valve, passes through the metering loop, and out past the injector valve shear-face rotor 15 where it moves into the conductivity cell chamber 27 just beyond the valve shear face. The presence of the leading edge of the sample is detected by a sudden increase in conductivity of the fluid in the cell. This change is converted by amplifier 22 to a logic level signal that is used by the control system 23 to stop the transfer pump motor 24.

The flush liquid and the air slug are invisible to the micro-conductivity cell. The unique construction of the conductive cell permits the advancing sample to be immediately recognized within the injector valve.

Figure 5:
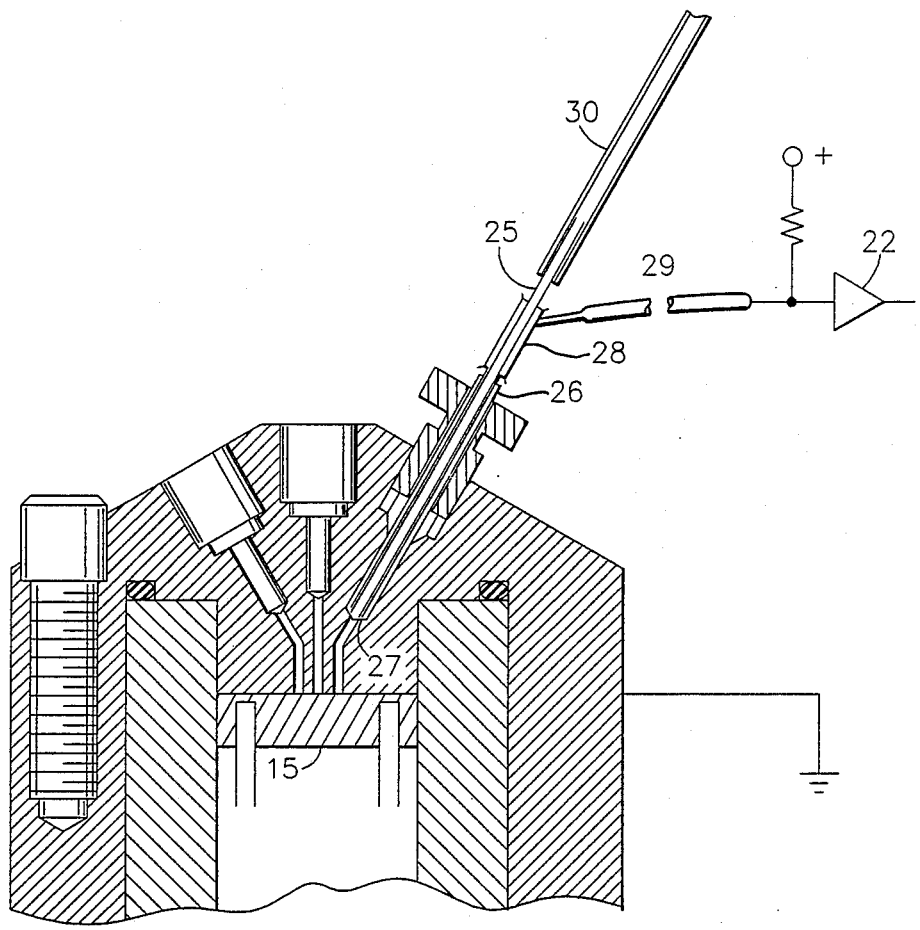
FIG. 5 is a sectional view of the valve, taken from the earlier disclosure, with the improved detector disclosed herein in place.

As will be seen in FIG. 5, the internal volume of the injector valve beyond the shear-face is quite small. Therefor, the amount of overfill required to insure a full metering loop is small—approximately five microliters.

During the cycle, the column pump remains connected to the chromatographic column via the bypass passage 17 of the injector valve as shown in FIG. 1A.

SAMPLE INJECTION

Figure 4:
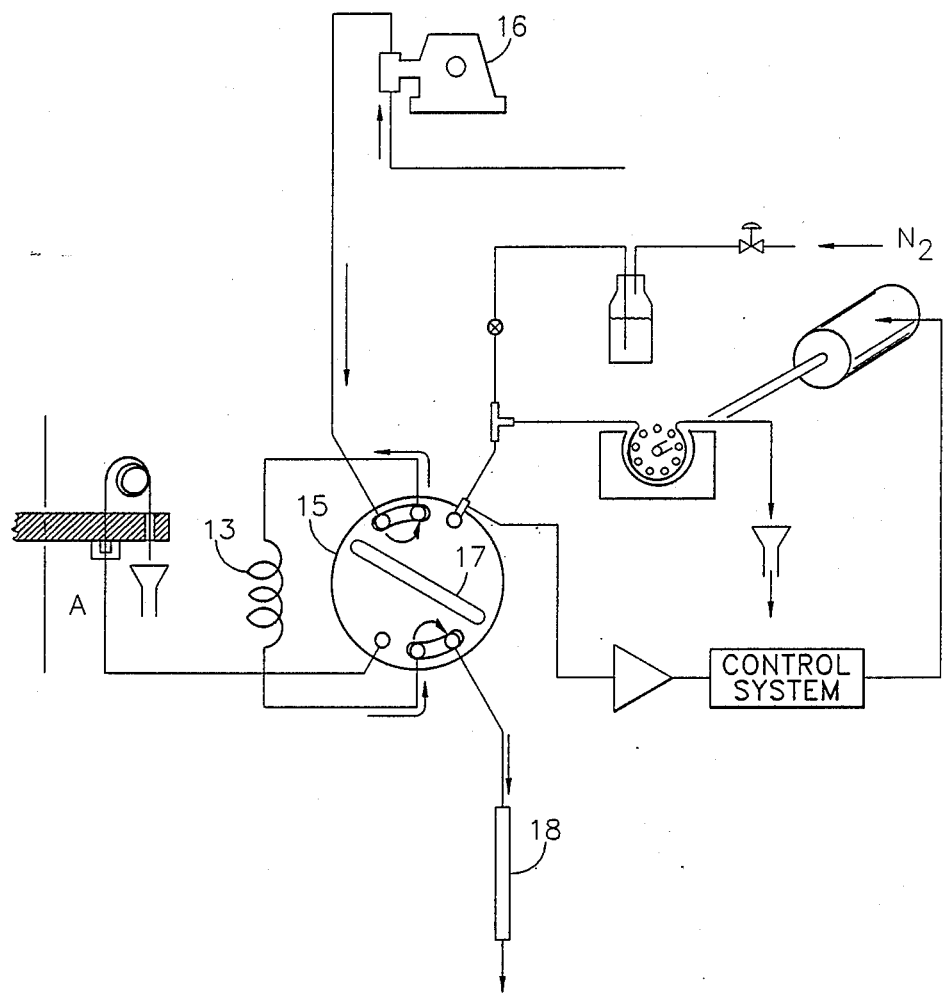
FIG. 4 is a partial schematic similar to FIG. 1A illustrating sample injection; and, FIG. 5 is a schematic section of the injection valve illustrating the particular cell construction that enables the determination of the leading edge of the sample passing from the sample trapping passageway of the rotor into a well of the valve stator.

With the sample in place in the injector loop, the shear-face rotor 15 of the valve V is now rotated to the position shown in FIG. 4. The bypass passage 17 is rotated out of contact with the injector valve ports, and the sample metering loop is now connected to these ports. The injector valve remains in this position only long enough for the sample to be swept out of the metering loop and on to the column. The shear-face rotor 15 then rotates back to the position shown in FIG. 1A through 3. The control program then repeats the system Flush and Dry cycles described above, in preparation for transferring and injecting the next sample.

CELL CONSTRUCTION

FIG. 5 shows the construction of the conductivity cell 27 and the manner by which it has been located within the injector valve, just beyond the shearface. The reader will understand that this is an improvement upon that valve claimed and described in Ogle et al. U.S. Pat. No. 4,444,066. Stainless steel (hypodermic)

capillary 25 enclosed within insulating capillary 26 is inserted into the injector valve effluent port and secured with a conventional capillary nut and gland assembly. Valve V is made of conducting material and electrically communicated to ground.

The conducting capillary 25 does not reach to the end of its insulating sheath and capillary 26. Hence, a microvolume conductivity cell 27 is formed within the injector valve body. The valve body, being of conductive metal, forms one electrode of the cell connected to circuit ground, while the hypodermic capillary 25 forms the opposite electrode of the cell. This electrode is connected by a conventional female electrical socket connector 28 to the electrical wire 29 leading to the input of buffer amplifier 22. Conventional nonconducting capillary 30 is forced over the hypodermic capillary to complete the effluent path from the injector valve to the sample transfer pump.

OTHER APPLICATIONS

The manner in which the cell is formed within the injector valve body is a function of the construction of the capillary assembly that replaces that which normally connects to the valve. This assembly, and its ensuing advantages, could be applied to any of several general purpose sample injector valves now on the market. Its application is restricted to the detection of conductive fluids.

It will be understood that we prefer a stainless steel capillary. It will be understood that other conductive members penetrating the valve well could also be used.

Further, we have chosen to improve the injection valve of Ogle et al. in U.S. Pat. No. 4,444,066. This valve includes a rotor and stator construction. It will be apparent that the valve construction utilized by this invention can be altered. For example, linearly sliding valve members can as well be used.

Prior art has employed time and rate of fluid flow to locate the limits of the sample aliquot as it is transferred into the metering loop. In order to assure that these limits safely extended beyond the shear faces of the injector valve, a comparatively large overfill (50 microliters) of sample was required. Using the detector and transfer system described here, the required overfill is reduced to five microliters. The two tables below demonstrate this improvement for the three metering loop volumes that are standard.

PRIOR ART

Time Duration—Required Overfill 50 Microliters

| Metering Loop | Required Sample | % Overfill |
|---|---|---|
| 100 microliters | 150 microliters | 50% |
| 50 microliters | 100 microliters | 100% |
| 20 microliters | 70 microliters | 250% |

PRESENT DISCLOSURE

Conductivity Detector—Required Overfill 5 Microliters

| Metering Loop | Required Sample | % Overfill |
|---|---|---|
| 100 microliters | 105 microliters | 5% |
| 50 microliters | 55 microliters | 10% |
| 20 microliters | 25 microliters | 25% |

In the high-sensitivity, small-volume applications which are of particular interest, the use of the sample presence detector has dramatically reduced the required overfill. This can become a critical consideration in those cases where sample availability is limited.

What is claimed is:

1. In a chromatographic circuit including a sample injector valve for use in injecting sequential samples into an analyzer system wherein said system includes: a sample source including a sample within a conductive fluid; a fluid source having a substantially nonconductive fluid; an analyzer column; the injector valve including a stationary housing and a moving valve member, said valve including conductive material at a first electrical potential; said stationary housing having a plurality of ports, said ports being in fluid communication respectively with said sample source, said fluid source and said analyzer column; said movable valve member mounted to said housing and defining a sample trapping passageway, said movable valve member movable from a first position wherein said sample trapping passageway is in fluid communication with said sample source to a second position wherein said sample trapping passageway is in fluid communication with said analyzer column; one of said ports of said housing constituting a registered port communicated to said sample passageway when said movable valve member is in said first position; a pump for pumping said sample through said sample trapping passageway towards said registered port; and means for stopping said pump responsive to said movement of said sample, the improvement in said means for stopping said pump comprising: a conductive member electrically isolated from said valve penetrating said registered port immediately adjacent said sample passageway, said conductive member at a second electrical potential; circuit detector means electrically communicated to said conductor member for detecting the presence of said sample upon entrance to said registered port; whereby sample upon first entrance to said registered port immediately stops said pump.

2. The invention of claim 1 and wherein said valve housing constitutes a stator and said moving valve member constitutes a rotor.

3. The invention of claim 1 and wherein said conductive member comprises a stainless steel capillary insulated from said valve housing.

4. A chromatographic apparatus comprising in combination: a sample source including a sample within a conductive fluid; a fluid source having a substantially nonconductive fluid; an analyzer column; an injector valve including a stationary housing and a moving valve member, said valve including conductive material at a first electrical potential; said housing defining a plurality of ports, said ports being in fluid communication respectively with said sample source, said fluid source and said analyzer column; said moveable valve member mounted for relative movement to said housing and defining a sample trapping passageway, said movable valve member movable from a first position where said sample trapping passageway is in fluid communication with said sample source to a second position wherein said sample trapping passageway is in fluid communication with said analyzer column, one of said ports of said stationary housing constituting a register port communicated to said sample trapping passageway when said movable valve member is in said first position; a conductive member penetrating said registered port immediately adjacent said sample trapping passageway, said conductive member insulated from said valve housing and maintained at a second electrical potential; a pump for pumping said sample through said sample trapping passsageway towards said registered port; circuit detector means electrically connected to said conductive member for detecting the presence of said sample at said conductive member immediately upon exit from said sample trapping passageway; means for stopping said pump responsive to said circuit detector means whereby sample entering into said registered port immediately stops; means for moving said movable valve member to the second position for injecting said sample into said analyzer column.

5. The apparatus of claim 4 and wherein said valve housing comprises a stator and said movable valve member includes a rotor, said rotor engaging said stator along a planar valve shear face.

6. The apparatus of claim 4 and wherein in said fluid source includes a rinsing fluid source of deionized water.

7. The apparatus of claim 4 and wherein said conductive member constitutes a stainless steel capillary, said stainless steel capillary placed within an immediately surrounding dielectric capillary, said dielectric capillary inserted into said registered port of said valve with said stainless steel capillary immediately adjacent to but not in contact with said valve body at said registered port.

8. A process for sequentially injecting samples into an analyzer column including the steps of providing a source of sequential samples; including samples within a conductive fluid; providing a fluid source having a substantially nonconductive fluid; providing the analyzer column; providing an injector valve constructed of conductive material including a housing and a moving valve member; defining ports in said housing in fluid communication respectively with said sample source, said fluid source and said analyzer column; defining in said movable valve member a sample trapping passageway; moving said movable valve member into a first position wherein said sample trapping passageway is in fluid communication with said sample source and registered to a registered port defined in said housing; inserting a conductive member penetrating into said registered port immediately adjacent said sample trapping passageway, said conductive member being insulated from said valve; pumping sample through said sample trapping passageway towards said registered port; detecting the electrical circuit between said valve on one hand and said conductive member on the other hand to determine the presence of the leading edge of said sample at said conductive member; stopping said pump responsive to said detecting step; and, moving said movable valve member to a second position in fluid communication with said analyzer column for injecting said sample to said analyzer column.

9. The process of claim 8 and wherein said fluid source includes rinse solution.

10. A sample injector valve for use in an analyzer system having a sample source, a buffer source, a measuring loop, an analyzer column and a rinse solution source, said injector valve comprising:
a housing including a conductive valve mechanism including a stator and a rotor;
said stator member mounted in said housing and having a plurality of ports, said ports being in fluid communication respectively with said sample source, said buffer source, said measuring loop; said analyzer column and said rinse solution source;
said rotor member mounted in said housing in juxtaposed relation with said stator member having a generally flat contact surface in contact with a generally flat surface of said stator member, said rotor member movable between a bypass and an injection position, one of said passageways constituting a sample trapping passageway being in fluid communication with said sample source in the bypass position of said rotor and with said column in the injection position of said rotor,
said stator member defining a registered port in fluid communication with said sample trapping passageway; said sample trapping passageway including a dielectric capillary threaded into said port to and towards said rotor;
a conductive capillary inserted interior of said dielectric capillary to and towards said rotor but short of contact with said conductive valve whereby sample passing in fluid to said conductive capillary can complete a circuit from said valve to said capillary; and detector means for indicating the presence of sample in said registered port.

11. In a sample injection valve, a detector for detecting the presence of an electrically conductive sample solution comprising:
a body defining a flow passage and a detection passage in flow communication with the flow passage, at least a portion of the flow passage having a wall that is conductive;
an electrode disposed along the detection passage and exposed to flow in the detection passage, the electrode being electrically insulated from the conductive portion of the flow passage wall; and
means for detecting electrical conduction between the electrode and the conductive portion of the flow passage wall upon the presence of the electrically conductive sample solution in the detection passage.

12. A detector as in claim 11 wherein the electrode is disposed along the detection passage closed to the flow passage so as to reduce the amount of sample solution required to fill the space between the end of the flow passage and the electrode along the detection passage to cause detection.

13. A detector as in claim 12 wherein the electrode is a conductive tube forming the detection passage which is insulated from the body.

14. A detector as in claim 13 wherein the flow passage is a metering passage which holds a desired amount of sample solution to be subsequently injected.

15. A sample injection valve for metering an electrically conductive sample solution to be injected comprising:
a valve body defining therein a sample metering passage and a detection passage in flow communication with the sample metering passage, at least a portion of the sample metering passage having a wall that is conductive;
an electrode attached to the valve body and exposed to flow through the detection passage, the electrode being electrically insulated from the conductive portion of the sample metering passage wall; and
means for detecting conduction through sample solution present between the electrode and the conductive portion of the sample metering passage upon the presence of sample solution in the detection passage.

16. A sample injection valve as in claim 15 wherein the electrode is disposed along the detection passage close to the sample metering passage so as to reduce the amount of sample solution required to fill the space between the end of the sample metering passage and the electrode along the detection passage to cause detection.

17. A sample injection valve as in claim 16 wherein the electrode is a conductive tube forming the detection passage which is insulated from the valve body.

18. A sample injection valve as in claim 15 wherein the valve body has ports to which the sample metering passage and detection passage are coupled, the valve body being conductive and the electrode is insulated from the valve body.

19. A sample injection valve as in claim 18 wherein the electrode is disposed close to the port for the detection passage so as to reduce the amount of sample solution required to fill the space between the end of the sample metering passage and the electrode to cause detection.

20. A sample injection valve as in claim 19 wherein the electrode is a conductive tube forming the detection passage which is insulated from the body.

* * * * *